United States Patent [19]

Strassberger

[11] 3,940,452

[45] Feb. 24, 1976

[54] ISOMERIZATION OF $C_{10}$-$C_{70}$ OLEFINS OF VINYLIDENE STRUCTURE TO OLEFINS OF VINYL STRUCTURE

[75] Inventor: Werner Strassberger, Gersthofen, Germany

[73] Assignee: Hoechst Aktiengesellschaft, Frankfurt am Main, Germany

[22] Filed: Aug. 15, 1974

[21] Appl. No.: 497,943

[30] Foreign Application Priority Data

July 6, 1974 Germany............................ 2432586

[52] U.S. Cl. ............................................ 260/683.2
[51] Int. Cl.² ............................................ C07C 5/30
[58] Field of Search .................................. 260/683.2

[56] References Cited
UNITED STATES PATENTS

| | | | |
|---|---|---|---|
| 2,603,591 | 7/1952 | Evans............................... | 260/683.2 |
| 3,448,164 | 6/1969 | Holm et al........................ | 260/683.2 |

FOREIGN PATENTS OR APPLICATIONS 549,139  11/1942  United Kingdom.............. 260/683.2

OTHER PUBLICATIONS

Hackh's Chemical Dictionary, 4th Ed. McGraw-Hill (1969) p. 199.

Primary Examiner—Delbert E. Gantz
Assistant Examiner—G. J. Crasanakis
Attorney, Agent, or Firm—Connolly and Hutz

[57] ABSTRACT

Olefins with vinyl groups are prepared by isomerization of olefins having vinylidene groups in the presence of a silicate having sheet structure, pumice or titanium dioxide as catalyst. The isomerization is carried out at a temperature of from 80 to 350°C and the starting long chain vinylidene olefins have 10 to 70 carbon atoms. The olefins with vinyl groups obtained can be used to manufacture waxy carboxylic acids, sulfonic acids and epoxides.

4 Claims, No Drawings

ISOMERIZATION OF $C_{10}$-$C_{70}$ OLEFINS OF VINYLIDENE STRUCTURE TO OLEFINS OF VINYL STRUCTURE

The present invention relates to a process for the manufacture of olefins having vinyl structure by isomerization of olefins having vinylidene structure.

It is known to transform linear or weakly branched aliphatic unsaturated hydrocarbons into olefins with high degree of branching. Isobutylene, a valuable starting material for alkylations and homo- and copolymerizations is prepared, for example, by catalytic isomerization of butene-1 in the gaseous phase at a temperature above 500°C in the presence of aluminum containing catalysts (cf. U.S. Pat. No. 3,558,733). In analogous manner iso-amylene, which is transformed into isoprene by dehydration, is produced from n-amylene. Isomerizations of the aforesaid type are also used for the manufacture of strongly branched, liquid olefins of high molecular weight, which are used, above all, in highly refined anti-knock motor fuels. The strongly branched olefins obtained by the known processes have the common characteristic of "internal" double bonds.

For other fields of application, especially as intermediates and starting materials for syntheses, olefins having a "terminal" double bond, so-called α-olefins are required. For the manufacture of emulsifiers or biologically degradable wash-active substances there are preferably used linear or weakly branched higher olefins having a vinyl double bond, which can be obtained by a special type of polymerization of ethylene using Ziegler catalysts. Products thus obtained are named "industrial α-olefins" but with regard to their double bonds they are not always uniform but contain, besides the desired vinyl double bonds, portions with transvinylene groupings and also olefins with vinylidene structure. When ethylene is oligomerized in the presence of a Ziegler catalyst the product obtained contains, as ascertained by infrared spectrum analysis, 65 to 68 % of vinyl double bonds (R-CH=CH$_2$), 25 to 30 % of vinylidene double bonds

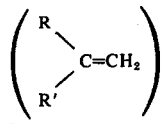

and 3 to 5 % of transvinylene double bonds

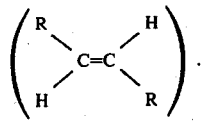

For many chemical reactions it is desirable or even necessary to use starting materials having as uniform as possible a structure, that is to say in the case of "industrial α-olefins" to use those having a very high degree of vinyl double bonds. In the oxidation of mixtures of olefin isomers with chromic acid carboxylic acids of uniform structure are only formed from the proportion of α-olefins, whereas the olefins with vinylidene double bond react in the first stage to yield ketones which then react further.

It is the object of the present invention to transform olefins having vinylidene structure into olefins with vinyl double bond, more particularly to reduce in inductrial α-olefin mixtures the content of vinylidene double bonds in the favor of vinyl double bonds.

The present invention therefore provides a process for the manufacture of olefins having vinyl structure from olefins having vinylidene structure by isomerization, which comprises heating olefins having vinylidene structure and containing from 10 to 70 carbon atoms at a temperature of from 80° to 350°C in the presence of a silicate having sheet structure, pumice or titanium dioxide as iosmerization catalyst.

By the process of the invention, which is very simple and can be carried out in a wide temperature range, higher olefins having vinylidene structure are transformed in favored manner and in a high yield into olefins having vinyl structure. It is surprising that the expected formation of a plurality of further isomers and, hence, of non uniform products does not take place.

As starting material for the process of the invention olefins having vinylidene structure and containing 10 to 70 and preferably 16 to 70 carbon atoms in the molecule are used. Preference is given to olefins, olefin mixtures or olefin fractions having from 10 to 70 carbon atoms in the molecule as obtained in the polymerization of ethylene in the presence of Ziegler type catalysts and containing a considerable proportion having vinylidene structure. Especially suitable are commercial grade mixtures of olefins having from 20 to 50 carbon atoms or 22 to 28 carbon atoms which generally contain 25 to 30 % of olefins with vinylidene double bonds.

Suitable isomerization catalysts are silicates with sheet structure, so-called phyllo-silicates or sheet silicates. Silicates of this type are those containing aluminum and/or magnesium which are substantially composed of two-dimensionally linked hexagons and in which the silicon-oxygen tetrahedral groups are linked by sharing one of every three oxygen atoms, and the ratio of silicon to oxygen is 2 : 5. Representatives of this group of silicates are, for example pyrophyllite, montmorillonite, talc, antigorite and kaolinite. Especially suitable are bleaching earths belonging to the group of montmorillonite, i.e. very finely divided hydrous aluminummagnesium silicates known by the name of fuller's earth, florida earth, or bentonite, as well as talc a hydroxyl group containing magnesium silicate. Pumice i.e. a hydrated alkali metal-alumina silicate and titanium dioxide are also suitable.

The isomerization catalysts are used in an amount of from 0.01 to 5.0, preferably 0.5 to 2.0 % by weight, calculated on the olefins, when working in liquid phase in a homogeneous system. Alternatively, columns or tubes filled with stationary catalyst can be used, through or over which the olefins to be isomerized are passed either in the form of a gas or in the molten state, optionally in continuous manner in a cycle. Whether the catalyst is used in the form of a powder, granules, shaped bodies or in pieces thus depends on the chosen working method. The isomerization can be carried without pressure as well as under pressure.

The isomerization temperature is in the range of from 80° to 350°C, preferably 100° to 280°C and more preferably 100° to 250°C, the reaction period generally being in the range of from about 10 minutes to approximately 2 hours.

According to a preferred embodiment the vinylidene hydrocarbons contained in industrial mixtures of higher α-olefins are isomerized by reacting the molten isomer mixture for about 1 hour at 120° to 200°C in a vessel with agitator with 1 % by weight of the powdery catalyst and separating the catalyst by filtration of the melt over a heated pressure filter.

By the process of the invention pure olefins having vinylidene structure as well as olefins of said structure contained in olefin mixtures can be isomerized on α-olefins in simple manner and in high yields. In the latter case products of better uniformity are obtained from structurally heterogeneous mixtures, which can be used, for example, for the manufacture of higher carboxylic acids, sulfonic acids, epoxides and the like.

The following examples illustrate the invention.

EXAMPLE 1

In a reactor equipped with stirrer and internal thermometer each time 500 grams of an olefin mixture resulting from a Ziegler synthesis and having 24 to 50 carbon atoms, in which 67.4 % of the double bonds had vinyl structure, 29.1 % had vinylidene structure and 3.5 % had transvinylene structure were isomerized under the conditions specified in the following table by heating with the respective catalyst in powder form. The isomerization products were freed from the catalyst by pressure filtration and analyzed by infrared spectrum analysis. It can be seen that the iodine number did practically not change while, depending on the catalyst and the working conditions used, 80 to 95 % of the vinylidene double bonds disappeared and were preferably transformed into vinyl double bonds the infrared bands of which are at 910 cm$^{-1}$. The infrared bands of the vinylidene double bond is found at 890 cm$^{-1}$ while the characteristic of the transvinylene double bond is a band at 965 cm$^{-1}$.

TABLE

| Example | treatment | double bonds in final product % | | | iodine number |
|---|---|---|---|---|---|
| | | vinyle | vinylidene | transvinylene | |
| 1 a | — | 67.4 | 29.1 | 3.5 | 46.0 |
| 1 b | 1 % bleaching earth[1] 60 minutes 120°C | 94.8 | 1.4 | 3.8 | 45.5 |
| 1 c | 1 % bleaching earth[1] 30 minutes 120°C | 93.7 | 1.8 | 4.5 | 45.7 |
| 1 d | 0.5 % bleaching earth[1] 60 minutes 150°C | 89.0 | 1.7 | 9.3 | 45.3 |
| 1 e | 1 % bleaching earth[1] 45 minutes 100°C | 92.6 | 2.3 | 5.1 | 44.8 |
| 1 f | 1 % talc 120 minutes 250°C | 93.0 | 1.6 | 5.4 | 45.7 |
| 1 g | 1 % talc 60 minutes 250°C | 89.9 | 4.2 | 5.9 | 45.3 |
| 1 h | 1 % kaolinite[3] 60 minutes 250°C | 90.2 | 3.7 | 6.1 | 45.2 |
| 1 i | 1 % pumice 60 minutes 250°C | 84.3 | 5.6 | 10.1 | 44.5 |

[1] Tonsil$^{(R)}$ Opt. of Messrs. Sud-Chemie, Munic.
[2] according to Kaufmann DGF-Einheitsmethoden C-V 11 b (53)
[3] Commercial China clay

EXAMPLE 2

In the apparatus described in Example 1, 500 g each of an olefin mixture having an iodine number of 66.4 and containing 22 to 26 carbon atoms in the molecule were isomerized as specified above. The reaction products were analyzed by infrared spectrum analysis. The results are listed in the following table.

| Example | treatment | double bonds in final product (%) | | |
|---|---|---|---|---|
| | | vinyle | vinylidene | transvinylene |
| 2 a | — | 70.2 | 28.3 | 1.5 |
| 2 b | 0.5 % bleaching earth[1] 60 minutes 120°C | 93.5 | 4.6 | 1.9 |
| 2 c | 1 % kaolinite 60 minutes 250°C | 92.8 | 3.6 | 3.6 |
| 2 d | 1 % titanium dioxide 60 minutes 150°C | 93.2 | 5.4 | 1.4 |

[1] Tonsil$^{(R)}$ Opt. of Messes Sud-Chemie, Munic

What is claimed is:

1. A process for the manufacture of olefins having vinyl structure from olefins with vinylidene structure by isomerization, which comprises heating an olefin having vinylidene structure and containing from 10 to 70 carbon atoms in the molecule at a temperature of from 80° to 350°C in the presence of a silicate having sheet structure, pumice, or titanium dioxide as isomerization catalyst.

2. The process of claim 1, wherein the isomerization catalyst is used in an amount of from 0.01 to 5.0 % by weight, calculated on the olefin.

3. The process of claim 1, wherein the olefin is passed in the liquid or vaporous state over or through the isomerization catalyst.

4. The process of claim 3, wherein the isomerization catalyst is bleaching earth.

* * * * *